(12) United States Patent
Türker et al.

(10) Patent No.: US 7,389,801 B2
(45) Date of Patent: Jun. 24, 2008

(54) FILLING SYSTEM FOR AN ANESTHETIC EVAPORATOR

(75) Inventors: Ahmet Türker, Lübeck (DE); Sven Pasdzior, Lübeck-Travemünde (DE); Dirk-Stefan Reichert, Lübeck (DE); Ernst-Günther Scharmer, Krummesse (DE); Grigory Kholtchanski, Lübeck (DE)

(73) Assignee: Drägerwerk Medical AG & Co. KG, Lübeck (DE)

( * ) Notice: Subject to any disclaimer, the term of this patent is extended or adjusted under 35 U.S.C. 154(b) by 103 days.

(21) Appl. No.: 11/419,338

(22) Filed: May 19, 2006

(65) Prior Publication Data

US 2007/0034284 A1 Feb. 15, 2007

(30) Foreign Application Priority Data

Aug. 11, 2005 (DE) .................. 10 2005 037 924

(51) Int. Cl.
*B65B 1/04* (2006.01)

(52) U.S. Cl. .................. 141/352; 141/292; 141/346; 141/363; 141/364; 141/365; 141/366; 251/321

(58) Field of Classification Search .............. 141/18, 141/285, 290–292, 319, 346–352, 382, 383, 141/363–366; 137/625.18; 251/321, 324, 251/229, 242–244
See application file for complete search history.

(56) References Cited

U.S. PATENT DOCUMENTS

| | | | | |
|---|---|---|---|---|
| 3,578,042 | A * | 5/1971 | Breiling | 141/301 |
| 5,381,836 | A * | 1/1995 | Braatz et al. | 141/21 |
| 5,419,316 | A * | 5/1995 | Bernstein | 128/203.12 |
| 5,687,777 | A * | 11/1997 | Dobson et al. | 141/18 |
| 5,832,972 | A * | 11/1998 | Thomas et al. | 141/360 |
| 5,915,427 | A * | 6/1999 | Grabenkort | 141/364 |
| 6,585,016 | B1 | 7/2003 | Falligant et al. | |
| 7,168,467 | B2 * | 1/2007 | Turker et al. | 141/292 |

* cited by examiner

*Primary Examiner*—Timothy L. Maust
(74) *Attorney, Agent, or Firm*—McGlew and Tuttle P.C.

(57) ABSTRACT

A filling system for an anesthetic evaporator allows an adapter neck (5) of a bottle adapter (1), which said adapter neck is coded in an anesthetic-specific manner, to be inserted into the filler neck of a filling device in a simple manner. A hinge (39) is provided between the adapter neck (5) and the threaded sleeve (2) of the bottle adapter (1).

19 Claims, 4 Drawing Sheets

FILLING SYSTEM FOR AN ANESTHETIC EVAPORATOR

CROSS REFERENCE TO RELATED APPLICATIONS

This application claims the benefit of priority under 35 U.S.C. § 119 of German Patent Application DE 10 2005 037 924.9 filed Nov. 8, 2005, the entire contents of which are incorporated herein by reference.

FIELD OF THE INVENTION

The present invention pertains to a filling system for an anesthetic evaporator.

BACKGROUND OF THE INVENTION

A filling system of the type has become known from U.S. Pat. No. 6,585,016 B1. To make it possible to fill liquid anesthetic into an anesthetic evaporator, a bottle adapter is necessary, which establishes the connection between the reservoir for liquid anesthetic and the filling device at the anesthetic evaporator. A threaded sleeve, which has two grooves for receiving an indexing ridge arranged at the neck of the reservoir, is provided at the bottle-side end of the bottle adapter. The indexing ridge has an anesthetic-specific design, so that only the bottle adapter fitting the reservoir can be screwed on the thread of the bottle.

An anesthetic-specific code in the form of two projections, which are arranged offset at an angle in relation to one another and mesh with corresponding recesses on the filler neck of the filling device, is also provided on the adapter neck of the bottle adapter.

The outlet connection of the bottle adapter is closed by means of a spring-loaded adapter valve, so that no anesthetic vapor can enter the environment. A corresponding filling valve is provided on the filling device. A stationary rod, whose length is selected to be such that when the adapter neck is introduced into the filler neck of the filling device, the adapter valve can be opened, is located in the middle of the filler neck of the filling device. The interplay of the bottle adapter and the filling device is designed such that the filling valve opens first and the adapter valve thereafter. Liquid anesthetic can then flow from the reservoir into the tank of the anesthetic evaporator.

The drawback of the prior-art filling system is that the anesthetic-specific code on the adapter neck can be introduced into the filler neck of the filling device in a certain preferred position only.

SUMMARY OF THE INVENTION

The basic object of the present invention is to simplify a filling system of the type in terms of its design in such a way that the adapter neck of the bottle adapter, which neck is coded in an anesthetic-specific manner, can be introduced into the filler neck in a simple manner.

According to the invention, a filling system for an anesthetic evaporator is provided comprising a bottle adapter for being connected to a reservoir for liquid anesthetic. The adapter has an adapter neck and a threaded sleeve for being connected to the reservoir. An anesthetic-specific code is provided on the adapter neck. A filling device is provided for filling anesthetic at the anesthetic evaporator. The filling device has a filler neck in an evaporator housing for receiving the adapter neck. An anesthetic-specific code is provided on the filler neck. This code has a design corresponding to that of the anesthetic-specific code on the adapter neck. A hinge connection is provided between the adapter neck and the threaded sleeve and/or the anesthetic-specific code on the filler neck and on the evaporator housing.

An insertion aid may be provided for centering the anesthetic-specific codes in the connection area between the bottle adapter and the filling device.

The advantage of the present invention is essentially that the anesthetic-specific codes can mesh without a torque due to the hinge connection between the bottle adapter and the filling device, without tilting occurring. When the bottle adapter is inserted into the filling device, the anesthetic-specific code on the adapter neck does not normally extend flush with the anesthetic-specific code on the filling device, so that the bottle adapter must be turned together with the reservoir in relation to the filling device until the codes come to lie flush over one another. If the position of the bottle adapter is changed when the codes are brought together, a torque develops between the bottle adapter and the filling device. The threaded sleeve of the bottle adapter can become detached from the connection thread of the reservoir as a result and leakage can develop. The hinge connection or pivoting connection provided according to the present invention prevents torque transmission between the bottle adapter and the filling device.

The hinge connection may be present either at the bottle adapter between the adapter neck and the threaded sleeve or on the filling device between the anesthetic-specific code on the filler neck and the evaporator housing. However, providing the hinge connection on both the bottle adapter and the filling device is also within the scope of the present invention.

An insertion aid, with which the anesthetic-specific codes can be aligned flush with one another, is advantageously provided in the connection area between the bottle adapter and the filling device. The insertion aid preferably comprises wedge-shaped intermediate spaces on the filler neck and bevels on the faces of the anesthetic-specific code on the bottle adapter, whose corner edges protrude into the intermediate spaces. The bottle adapter is centered as a result in relation to the filler neck.

An exemplary embodiment of the present invention is shown in the figure and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
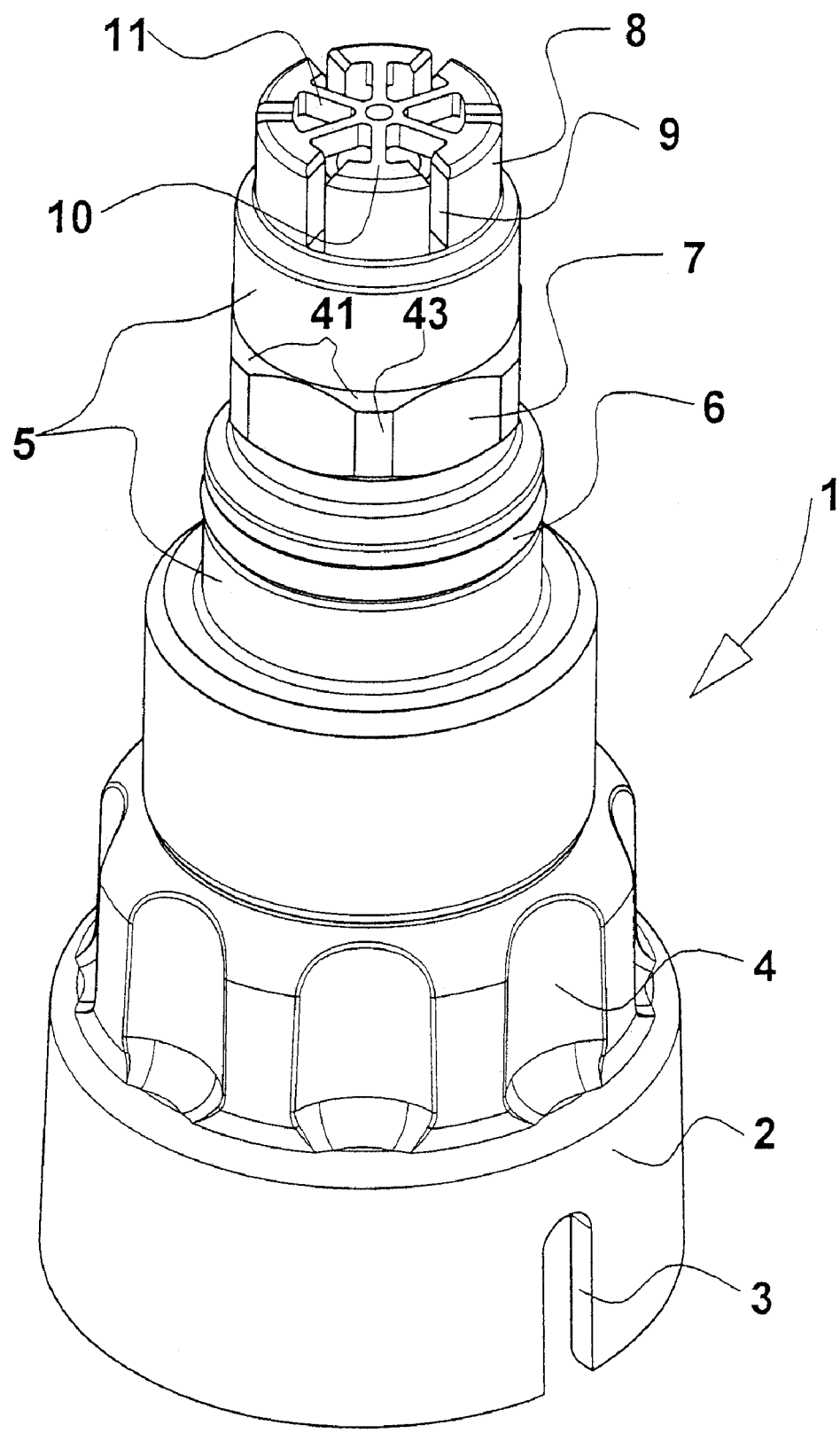
FIG. 1 is a perspective view showing a bottle adapter according to the invention.

Referring to the drawings in particular, FIG. 1 shows a perspective view of a bottle adapter 1, which has on its underside a threaded sleeve 2 for screwing on a reservoir for liquid anesthetic, which is not shown in FIG. 1. The reservoir has, on its bottle collar, an anesthetic-specific indexing ridge, which is inserted into receiving grooves 3 of the threaded sleeve 2. Thus, only a bottle adapter 1 that belongs to the anesthetic can be screwed onto the reservoir. The screwing motion is facilitated here by recessed grips 4 above the threaded sleeve 2. An adapter neck 5 with an O-ring 6 and with an outer polygon 7 for anesthetic-specific code as well as an outlet connection 8 with radially extending slots 9 are located at the top end of the bottle adapter 1. The top side 10 of the connection is designed as a star-shaped body 11. The faces 41 of the outer polygon 7 are provided with a bevel 43.

Figure 2:
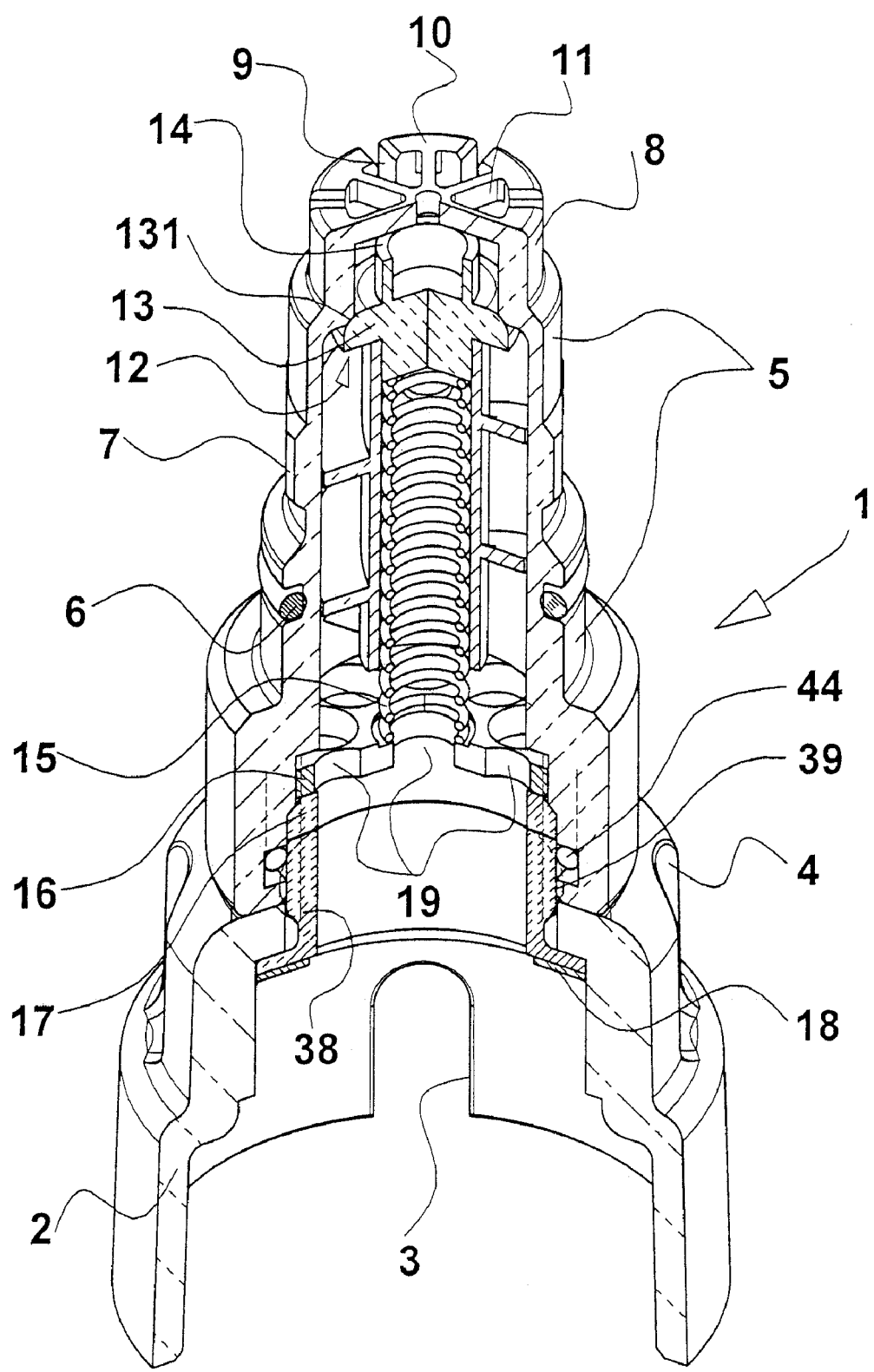
FIG. 2 is a longitudinal sectional view of the bottle adapter according to FIG. 1.

FIG. 2 illustrates the bottle adapter 1 according to FIG. 1 in a longitudinal section. Identical components are designated by the same reference numbers as in FIG. 1. A shut-off valve 12 with a valve piston 13, with a ring body 14 on the top side of the valve piston 13 and with a valve spring 15, which is pretensioned by means of a support plate 16 and presses the valve piston 13 against a sealing surface 131, is located within the bottle adapter 1. The support plate 16 is held within the bottle adapter 1 by a threaded ring 17. A sealing ring 18, which is in contact with the bottle neck of the reservoir, which is not shown in the figures, is fastened on the underside of a sleeve 38. The support plate 16 contains holes 19, via which the gas and liquid exchange takes place. The polygon 7 has an anesthetic-specific design, for example, a hexagon for halothane, a regular pentagon for enflurane, a regular heptagon for isoflurane. The sleeve 38 is in contact with the inner side of the adapter neck 5 and forms a hinge or pivot structure 39 together with the adapter neck 5. The hinge 39 is sealed with a sealing ring 44 arranged between the adapter neck 5 and the sleeve 38.

Figure 3:
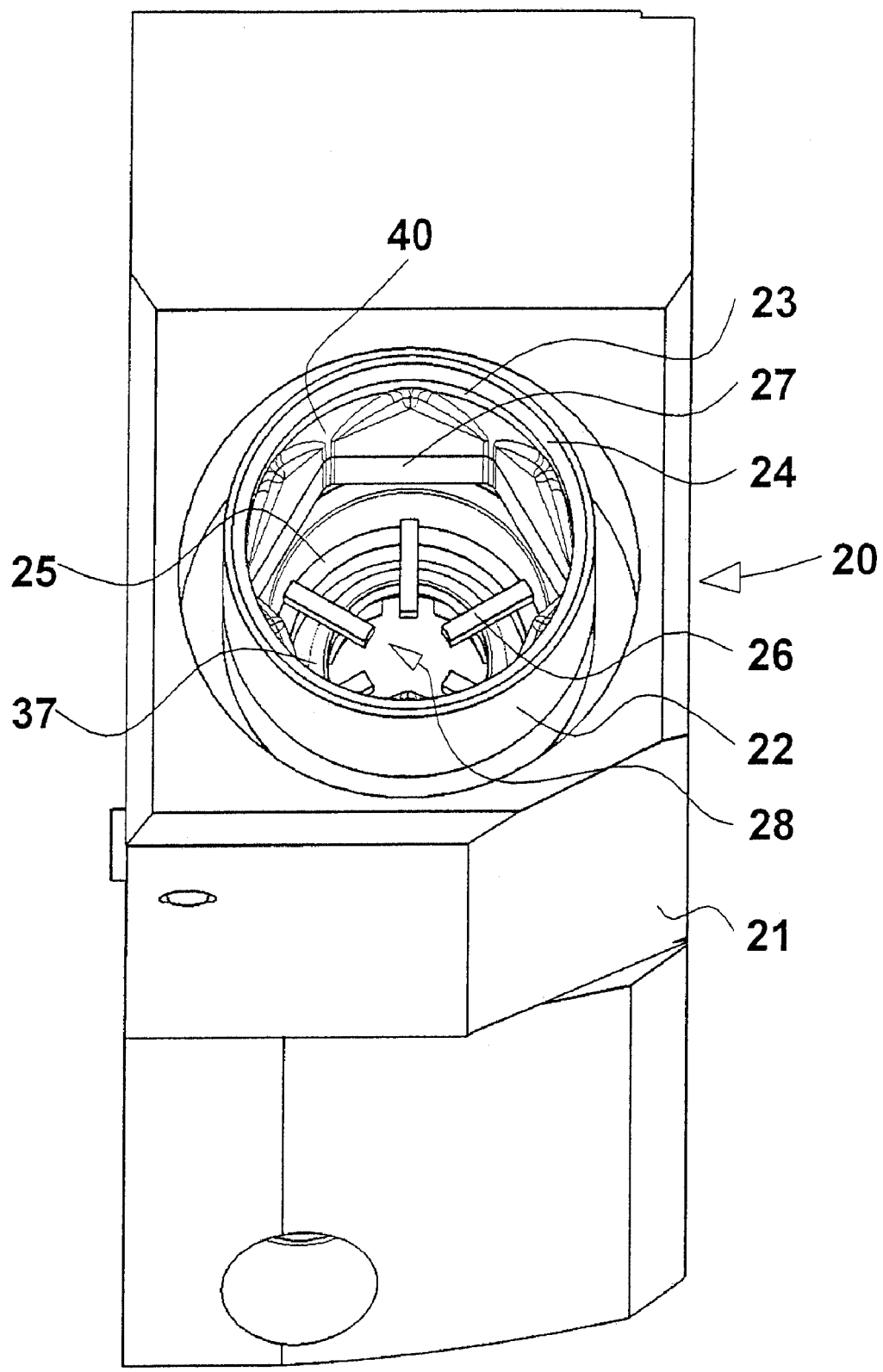
FIG. 3 is a perspective view of a filling device according to the invention.

FIG. 3 shows a perspective view of a filling device 20 for anesthetics on an anesthetic evaporator 21. The filling device 20 has a filler neck 22 with a cylindrical sealing surface 23, an inner insertion bevel 24 at the upper part of the filler neck 22, a spoked wheel 25 with radially inwardly pointing spokes 26, an inner polygon 27 for the anesthetic-specific code, and a filling valve 28. The flat surfaces of the inner polygon 27 are extended in a wedge-shaped manner in the direction of the insertion bevel 24. Intermediate spaces 40 are formed by the wedge-shaped extension.

Figure 4:
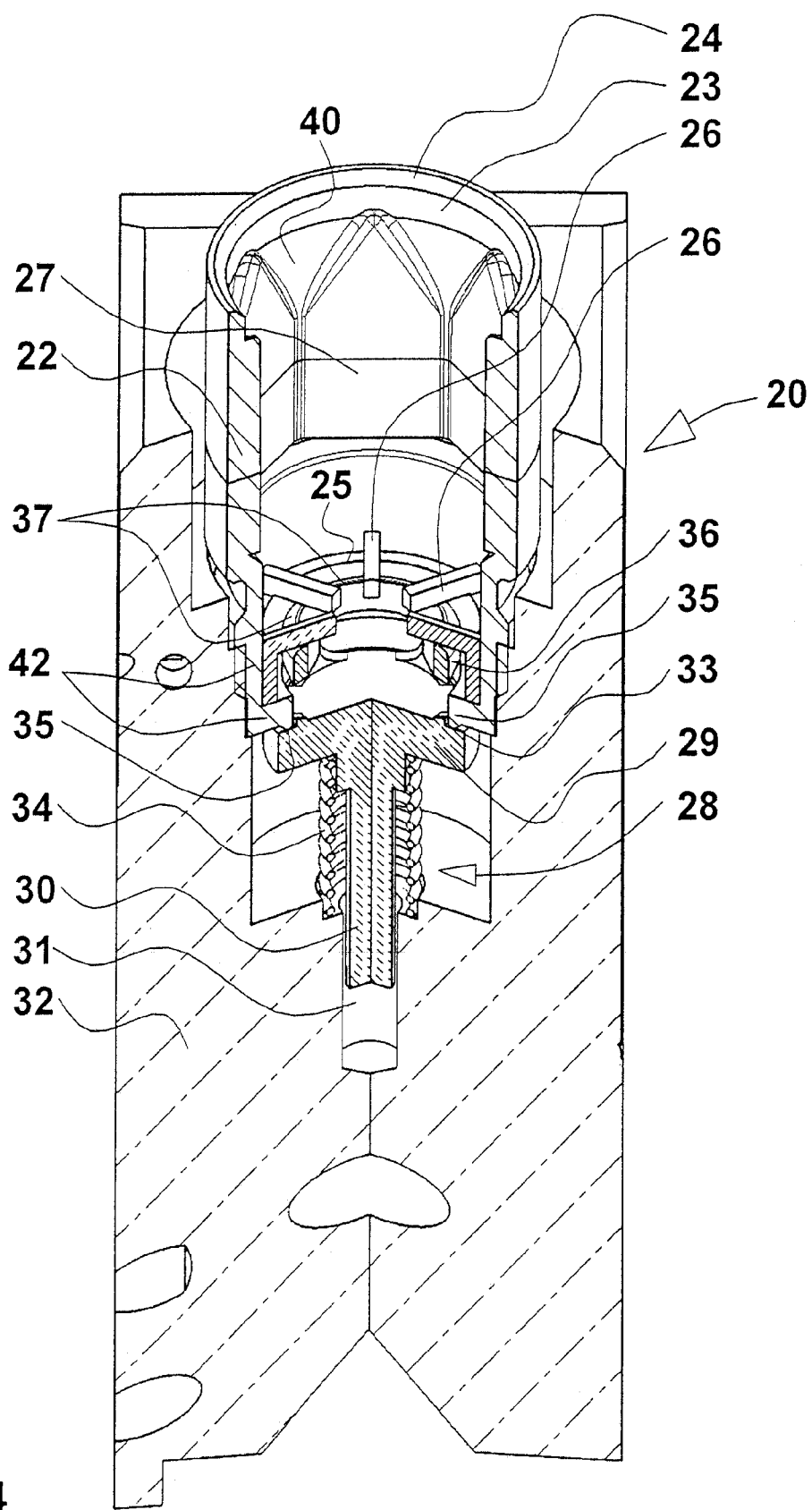
FIG. 4 is a longitudinal sectional view of the filling device according to FIG. 3.

FIG. 4 illustrates the filling device 20 in a longitudinal section. Identical components are designated by the same reference numbers as in FIG. 3. The filling valve 28 comprises a valve plate 29 at a valve guide rod 30, which is received in a hole 31 of the evaporator housing 32 in such a way that it can perform stroke motions. The top side 33 of the valve plate 29 is pressed by means of a valve spring 34 against a sealing crater 35 of the filling valve 28. A guide ring 36 is connected to the valve plate 29 and is displaceable together with the valve plate 29. The filler neck 22 is connected to the evaporator housing 32 via a hinge or pivot structure 42.

The filling system according to the present invention operates as follows:

When the bottle adapter 1 is inserted into the filling device 20, the faces 41 with the bevels 43 will first enter the area of the intermediate spaces 40 of the inner polygon 27. The corner edges of the bevels 43 are located in the wedge-shaped intermediate spaces 40 and the adapter neck 5 is thus centered in relation to the filler neck 22 due to restricted guidance. A possible angular offset is compensated by means of the hinges 39, 42. The spokes 26 are then located in the slots 9 of the outlet connection 8 and the outlet connection 8 enters the area of the guide ring 36.

By pressing the bottle adapter 1, the connection top side 10 of the bottle adapter is in contact with the top side 37 of the guide ring 36 and the filling valve 28 opens. The adapter valve 12 is still closed. If the pressure on the bottle adapter 1 is increased further, the valve plate 29 is displaced further downward against the force of the valve spring 34 and the spokes 26 touch the ring body 14 of the valve body 13, as a result of which the adapter valve 12 opens. Anesthetic will now flow from the reservoir via the holes 19 of the support plate 16 into the tank of the anesthetic evaporator and, as in communicating vessels, gas flows back into the reservoir from the tank via the holes 19.

When the filling operation is terminated, the adapter valve 12 will first close, so that possible residual quantities of anesthetic within the filler neck 22 can flow off into the tank of the anesthetic evaporator 21. The filling valve 28 is then closed and the bottle adapter 1 can be removed from the filler neck 22. If the reservoir is turned in relation to the filling device 20, the threaded sleeve 2 remains rigidly connected to the connection thread of the reservoir, because no torques can be transmitted via the hinges 39, 42.

While specific embodiments of the invention have been shown and described in detail to illustrate the application of the principles of the invention, it will be understood that the invention may be embodied otherwise without departing from such principles.

What is claimed is:

1. A filling system for an anesthetic evaporator, the filling system comprising:
    a bottle adapter for being connected to a reservoir for liquid anesthetic, the bottle adapter having an adapter neck and a threaded sleeve for being connected to the reservoir, said adapter neck having an inner adapter neck surface and an outer adapter neck surface, said sleeve being in contact with said inner adapter neck surface;
    an outer polygonal element defining an outer anesthetic-specific code portion on the adapter neck, said outer polygonal element engaging said outer adapter neck surface;
    a filling device for anesthetic at the anesthetic evaporator, the filling device including a filler neck in an evaporator housing for receiving the adapter neck, said filler neck having an inner filler neck surface;
    an inner polygonal element defining an inner anesthetic-specific code portion on the filler neck, said inner polygonal element being located on an inner surface of said filler neck, said inner anesthetic-specific code portion having a design corresponding to that of the outer polygonal element on the adapter neck such that said outer polygonal element is arranged within said inner polygonal element when said adapter neck is inserted into said filling neck; and
    a hinge connection disposed one of between said adapter neck and said threaded sleeve and between said inner anesthetic-specific code portion on said filler neck and said evaporator housing.

2. A filling system in accordance with claim 1, further comprising an insertion aid for centering the anesthetic-specific code portions, said insertion aid being provided in a connection area between said bottle adapter and said filling device.

3. A filling system in accordance with claim 1, further comprising:
    a filling valve arranged in said filler neck;
    an adapter valve arranged in said adapter neck, said adapter neck having a top surface defining a plurality of slots;
    a plurality of bars extending radially inward from said inner surface of said filler neck, each slot of said adapter neck receiving one of said bars when said adapter neck is inserted in said filler neck, said bars, said adapter neck, said adapter valve and said filling valve being arranged such that said adapter neck opens said filling valve and said bars open said adapter valve when said adapter neck is inserted into said filler neck.

4. A filling system in accordance with claim 1, wherein said adapter neck includes an adapter valve and said filler neck includes a filling valve.

5. A filling system in accordance with claim 1, wherein said inner and outer polygonal elements are designed as n-sided polygons.

6. A filling system in accordance with claim 5, wherein said inner and outer polygonal elements are one of a hexagon, a pentagon or a heptagon.

7. A filling system for an anesthetic evaporator, the filling system comprising:
  a bottle adapter for connection to a reservoir for liquid anesthetic, the bottle adapter having an adapter neck with an outer polygonal element on an outer surface thereof, said outer polygonal element defining an anesthetic-specific portion and having a sleeve for connection to the reservoir, said adapter neck being connected to said sleeve with a sleeve to adapter neck connection;
  a filling device for anesthetic at the anesthetic evaporator, the filling device including a filler neck with an inner polygonal element on an inner surface thereof, said inner polygonal element defining an anesthetic-specific portion, said filler neck being connected to said anesthetic evaporator with a housing to filler neck connection, one of said sleeve to adapter neck connection and said housing to filler neck connection comprising a pivotable connection allowing relative angular movement between said evaporator housing and said filler neck or between said sleeve and said adapter neck, said inner polygonal element engaging said outer polygonal element when said filling device receives said adapter neck.

8. A filling system in accordance with claim 7, wherein the other of said sleeve to adapter neck connection and said housing to filler neck connection comprises a pivotable connection allowing relative angular movement between said evaporator housing and said filler neck or between said sleeve and said adapter neck.

9. A filling system in accordance with claim 7, further comprising an insertion aid for centering the anesthetic-specific code portion of said filler neck of said filling device and the anesthetic-specific code of said adapter neck, said insertion aid being provided in a connection area between said bottle adapter and said filling device.

10. A filling system in accordance with claim 7, further comprising:
  a filling valve arranged in said filler neck;
  an adapter valve arranged in said adapter neck, said adapter neck having a top surface defining a plurality of slots;
  a plurality of bars extending radially inward from said inner surface of said filler neck, each slot of said adapter neck receiving one of said bars when said adapter neck is inserted in said filler neck, said bars, said adapter neck, said adapter valve and said filling valve being arranged such that said adapter neck opens said filling valve and said bars open said adapter valve when said adapter neck is inserted into said filler neck.

11. A filling system in accordance with claim 7, wherein said adapter neck includes an adapter valve and said filler neck includes a filling valve.

12. A filling system in accordance with claim 7, wherein said inner and outer polygonal elements are designed as n-sided polygons.

13. A filling system in accordance with claim 12, wherein said inner and outer polygonal elements are one of a hexagon, a pentagon or a heptagon.

14. A filling system for an anesthetic evaporator, the filling system comprising:
  a bottle adapter for connection to a reservoir for liquid anesthetic, the bottle adapter having an adapter neck with an external surface defining outer anesthetic-specific polygon surface portions and having a sleeve for connection to the reservoir, said adapter neck being connected to said sleeve with a sleeve to adapter neck connection allowing relative angular movement between said sleeve and said adapter neck;
  a filling device for anesthetic at the anesthetic evaporator, the filling device including a filler neck with an inner filler neck surface defining inner anesthetic-specific polygon surface portions, said inner anesthetic-specific polygon surface portions defining a plurality of outer anesthetic-specific polygon surface receiving recesses, said filler neck being connected to said anesthetic evaporator with a housing to filler neck connection allowing relative angular movement between said evaporator housing and said filler neck, each outer anesthetic-specific polygon surface receiving recess receiving one of said outer anesthetic-specific polygon surface portions when said adapter neck is inserted into said filler neck.

15. A filling system in accordance with claim 14, further comprising an insertion aid for centering the anesthetic-specific code portion of said filler neck of said filling device with the anesthetic-specific code portion of said adapter neck, said insertion aid being provided in a connection area between said bottle adapter and said filling device.

16. A filling system in accordance with claim 14, further comprising:
  a filling valve arranged in said filler neck;
  an adapter valve arranged in said adapter neck, said adapter neck having a top surface defining a plurality of slots;
  a plurality of bars extending radially inward from said inner surface of said filler neck, each slot of said adapter neck receiving one of said bars when said adapter neck is inserted in said filler neck, said bars, said adapter neck, said adapter valve and said filling valve being arranged such that said adapter neck opens said filling valve and said bars open said adapter valve when said adapter neck is inserted into said filler neck.

17. A filling system in accordance with claim 14, wherein said adapter neck includes an adapter valve and said filler neck includes a filling valve.

18. A filling system in accordance with claim 14, wherein said inner anesthetic-specific polygon surface portions and said outer anesthetic specific polygon surface portions form n-sided polygons.

19. A filling system in accordance with claim 18, wherein said inner anesthetic-specific polygon surface portions and said outer anesthetic specific polygon surface portions form one of a hexagon, a pentagon or a heptagon.

\* \* \* \* \*